United States Patent [19]

De Fusco et al.

[11] Patent Number: 4,531,013

[45] Date of Patent: Jul. 23, 1985

[54] PREPARATION OF A DIAMINOTETRANITRONAPHTHALENE

[75] Inventors: Albert A. De Fusco; Arnold T. Nielsen, both of Ridgecrest, Calif.

[73] Assignee: The United States of America as represented by the Secretary of the Navy, Washington, D.C.

[21] Appl. No.: 637,634

[22] Filed: Aug. 3, 1984

[51] Int. Cl.$^3$ .............................................. C07C 87/66
[52] U.S. Cl. .................... 564/428; 564/411; 564/441; 149/105
[58] Field of Search ............... 564/411, 414, 428, 441; 149/105

[56] References Cited

U.S. PATENT DOCUMENTS

| | | | |
|---|---|---|---|
| 2,012,985 | 9/1935 | Castner | 260/142 |
| 2,256,999 | 9/1941 | Castner | 260/645 |
| 2,824,884 | 2/1958 | Barnhart et al. | 260/404 |
| 2,895,826 | 7/1959 | Salminen et al. | 96/55 |
| 3,145,235 | 8/1964 | Ashton | 564/428 |
| 3,187,048 | 6/1965 | Burgdorf | 260/578 |
| 3,188,346 | 6/1965 | Kalopssis | 260/577 |
| 3,255,247 | 6/1966 | Olin | 260/562 |
| 4,151,203 | 4/1979 | Cheng | 260/582 |

OTHER PUBLICATIONS

Wagner & Zook "Synthetic Organic Chemistry" pp. 675–677 (1953).
Friedman, Fishel & Schechter"J. of Org. Chem." vol. 30 (1965), pp. 1453–1456.
H. H. Hodgson and J. S. Whitehurst, *The Tetrazotisation of 1:5- and 1:8- naphthalene diamines and Tetranitration of 1:5- and 1:8 di p toluenesulphon amidonaphthalenes,* Chemical Soc'y, London J., pp. 80–81 (1947).

*Primary Examiner*—Helen M. S. Sneed
*Assistant Examiner*—John A. Sopp
*Attorney, Agent, or Firm*—Robert L. Beers; W. Thom Skeer; Shelley G. Precivale

[57] ABSTRACT

A new compound 2,6-diamino-1,4,5,8-tetranitronaphthalene is disclosed and a method of preparation thereof. The new compound is useful as a high energy, high density explosive.

16 Claims, No Drawings

PREPARATION OF A DIAMINOTETRANITRONAPHTHALENE

BACKGROUND OF THE INVENTION

1. Field of the Invention

This invention relates to a composition of matter and a method for producing the same, and is particularly related to a compound 2,6-diamino-1,4,5,8-tetranitronaphthalene, useful as an explosive.

2. Description of the Prior Art

The compound 2,6-diamino-1,4,5,8-tetranitronaphthalene is of great interest to those concerned with explosives. Aryl compounds having large numbers of nitro groups on the rings are well known as explosives. A typical example is trinitrotoluene which is more commonly known simply as TNT. H. H. Hodgson and J. S. Whitehurst report the isomeric compounds 1,5-diamino-2,4,6,8-tetranitronaphthalene and 1,8-diamino-2,4,5,7-tetranitronaphthalene in *The Tetrazotisation of 1:5- and 1:8-naphthalene diamines and Tetranitration of 1:5- and 1:8-di-p-toluenesulphonamidonaphthalenes*, Chemical Soc'y, London J., pp. 80–81 (1947). However, the authors of this specification were unable to duplicate the results of the English authors. Accordingly, the authors of this specification, after a considerable amount of experimentation, developed the hereinafter disclosed method for the preparation of 2,6-diamino-1,4,5,8-tetranitronaphthalene.

SUMMARY OF THE INVENTION

According to this invention, 2,6-diamino-1,4,5,8-tetranitronaphthalene is prepared by starting with 2,6-dimethylnaphthalene which is converted into the 2,6-naphthalene dicarboxylic acid by a known reaction. This solid acid is then added to $HNO_3$ and the solution filtered to yield a solid dinitro product 1,5-dinitro-3,7-naphthalene dicarboxylic acid. A suspension of this solid is formed with the addition of fuming $H_2SO_4$ and 1,2-dichloroethane. Solid $NaN_3$ is then added to the suspension, and the mixture subsequently neutralized with aqueous NaOH. The solution is then filtered to yield a solid 3,7-diamino-1,5-dinitronaphthalene. This solid is added to trifluoroacetic anhydride, refluxed and filtered to yield a solid 1,5-dinitro-3,7-di(trifluoroacetamido) naphthalene. A suspension of this solid is formed with the addition of $HNO_3$ and $H_2SO_4$. Precipitation yields a solid 2,6-di(trifluoroacetamido)-1,4,5,8-tetranitronaphthalene. A suspension of this solid and methanol is made and dry hydrogen chloride bubbled through. Methanol is removed and the remaining powder is the desired end product 2,6-diamino-1,4,5,8-tetranitronaphthalene, having the following structure:

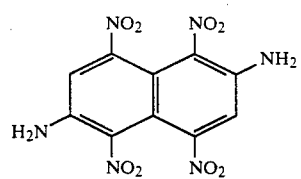

DESCRIPTION OF THE PREFERRED EMBODIMENT

The compound 2,6-diamino-1,4,5,8-tetranitronaphthalene may be prepared by carrying out the six-step procedure set forth in the following specific example.

EXAMPLE

Step 1

Preparation of 2,6-naphthalene dicarboxylic acid

The starting material is 2,6-dimethylnaphthalene. This is converted into the 2,6-naphthalene dicarboxylic acid by a known reaction, using aqueous sodium dichromate (VI). See L. Friedman, D. L. Fisheland, and H. Shechter, *Oxidation of Alkylarenes with Aqueous Sodium Dichromate. A Useful Method for Preparing Mono- and Polyaromatic Carboxylic Acids*, J. Organic Chemistry 30, p. 1453 (1965).

Step 2

Preparation of 1,5-dinitro-3,7-naphthalene dicarboxylic acid

Solid 2,6-naphthalene dicarboxylic acid (57.4 g, 0.27 moles) is added portionwise to mechanically stirred 90% $HNO_3$ (700 ml) at 25° C. During addition, the temperature of the reaction mixture rises to 36° C. as the starting material dissolves. After addition is completed, the reaction mixture is heated to 60° C. over a one hour period and is maintained at that temperature for an additional one hour. After cooling to ambient temperature, the reaction mixture is poured over 1800 g of ice and then filtered. The remaining solid product is washed with 200 ml of $H_2O$ four times. The dinitro product (51.6 g, 64% yield) is dried in vacuo at ambient temperature and has a melting point of 357° C. with decomposition. An $^1NMR$ (DMSO -$d_6$) spectrum shows peaks at δ9.62 (2H, d, J≃1 Hz, ArH) and 9.28 (2H, d, J≃1 Hz, ArH). Analysis calculated for $C_{12}H_6N_2O_8$: C, 47.07; H, 1.98; N, 9.15. Found: C, 47.16; H, 1.87; N, 9.01.

Step 3

Preparation of 3,7-diamino-1,5-dinitronaphthalene

A suspension of 50 g (0.16 moles) of 1,5-dinitro-3,7-naphthalene dicarboxylic acid in 400 ml of 18–24% fuming $H_2SO_4$ and 150 ml of 1,2-dichloroethane is cooled to 3° C. Solid $NaN_3$ (26.6 g, 0.41 moles) is cautiously and slowly added portionwise to the cooled suspension so as not to allow the temperature of the reaction mixture to go above 8° C. After addition is complete, the reaction mixture is allowed to reach ambient temperature without removal from the cooling bath and then heated to 50° C. for one hour. The mixture is then cooled to approximately 15° C., poured over 6000 g of ice and then neutralized with 870 ml of 50% aqueous NaOH. The resulting purple precipitate is removed by filtration and then washed with a sufficient amount of hot water to afford 32 g (80% yield) of product having a melting point of 350° C. (decomposition), after drying in vacuo at room temperature. An $^1H$ NMR (DMSO -$d_6$) spectrum displays peaks at δ7.85 (2H, d, J≃2 Hz, ArH). An IR (KBr) spectrum shows peaks at 3310, 3400 ($NH_2$ doublet) and 1520 ($NO_2$) cm$^{-1}$. Analysis calculated for $C_{10}H_8N_4O_4$: C, 48.39; H, 3.25; N, 22.58. Found: C, 48.41; H, 3.38; N, 22.62.

Step 4

Preparation of 1,5-dinitro-3,7-di(trifluoroacetamido) naphthalene

Solid 3,7-diamino-1,5-dinitronaphthalene (30 g, 0.12 moles) is added portionwise to 125 ml of chilled trifluoroacetic anhydride. The resulting suspension is refluxed for two days, cooled and filtered. The product is dried in vacuo over $CaSO_4$ to afford 47.2 g (89% yield) of 1,5-dinitro-3,7-di(trifluoroacetamido) naphthalene, having a melting point of 350° C. (decomposition). A sample is recrystallized from $CH_3CN$ to afford an analytically pure product. The $^1H$ NMR (DMSO -$d_6$) spectrum shows peaks at $\delta$9.30 (2H, d, ArH), 9.05 (2H, d, ArH) and 12.10 (2H, br s, NH). The Ir (KBr) spectrum shows peaks at 3225 (NH), 1730 (C=O), 1610 (C=C), 1550, 1515 ($NO_2$), 1340, 1300, 1275, 1225 (C—F), 1200, 1175, 1125 ($NO_2$), 940, 895, 880, 750 and 725 $cm^{-1}$. Analysis calculated for $C_{14}H_6N_4O_6F_6$: C, 38.20; H, 1.37; N, 12.73; F, 25.89. Found: C, 38.33; H, 1.36; N, 12.79; F, 25.75.

Step 5

Prepatration of 2,6-di(trifluoroacetamido)-1,4,5,8-tetranitronaphthalene

A solution of 6.2 ml of 90% $HNO_3$ and 3.8 ml of 97% $H_2SO_4$ is added dropwise over a 15 minute period to a stirring suspension of 6.0 g (0.0136 moles) of 1,5-dinitro-3,7-di(trifluoroacetamido) naphthalene and 50 ml of 97% $H_2SO_4$ at room temperature. During addition, the temperature of the reaction rises to 36° C. After addition is completed, the reaction mixture is heated to 55° C. for two hours, allowed to cool to room temperature and is then poured over 900 g of ice. The precipitate is filtered through a coarse sintered glass funnel with gentle suction and then washed with $H_2O$ until the washings remain clear. The remaining solid is then dried in vacuo to obtain 6.51 g (90% yield) of product as a microcrystalline solid having a melting point of 290°-292° C. (decomposition). The crude product is recrystallized from 700 ml of ethyl acetate to afford a total (from several crops) of 4.33 g (60% yield) of product having a melting point of 319° C. (decomposition). The $^1H$ NMR (acetone -$d_6$) spectrum shows peaks at $\delta$11.33 (2H, br s, NHCO) and 9.35 (2H, s, ArH). The IR (KBr) spectrum peaks at 3300 (NH), 1750 (C=O), 1610 (C=C), 1540, 1520, 1460, 1350, 1310, 1300, 1250, 1200, 1175, 1140, 1025, 940, 910, 895, 860, 770, 750 and 735 $cm^{-1}$. Analysis calculated for $C_{14}H_4N_6O_{10}F_6$: C, 31.71; H, 0.76; N, 15.85; F, 21.50. Found: C, 31.90; H, 0.80; N, 15.64; F, 21.49.

Step 6

Preparation of 2,6-diamino-1,4,5,8-tetranitronaphthalene

Dry hydrogen chloride is bubbled, over a three hour period, into a stirring suspension of 5.0 g (0.0094 moles) of 2,6-di(trifluoroacetamido)-1,4,5,8-tetranitronaphthalene and 500 ml of methanol at room temperature. During addition of HCl, the temperature of the reaction mixture is allowed to rise freely to approximately 50° C. After addition is completed, the methanol is removed under reduced pressure with a warm water bath. The remaining residue is treated with 300 ml of water and the resulting suspension is stirred until a finely divided powder is present. The solid is filtered, washed thoroughly with water and then dried in vacuo to afford 3.12 g (98% yield) of product having a melting point of 280° C. (decomposition). The $^1H$ NMR (acetone -$d_6$/DMSO -$d_6$, 1/1, v/v) spectrum shows peaks at $\delta$9.23 (2H, s, ArH) and 8.93 (4H, br s, $NH_2$). The IR spectrum shows peaks at 3300 (d, $NH_2$), 1610 (C=C), 1530 ($NO_2$), 1350, 1320, 1250 ($NO_2$), 865 and 760 $cm^{-1}$. A small sample is crystallized from $CH_3CN$ for elemental analysis and has a melting point of 297° C. (decomposition). However, extensive decomposition occurs and only very small amounts of product are recoverable from crystallization. Analysis calculated for $C_{10}H_6N_6O_8$: C, 35.52; H, 1.79; N, 24.85. Found: C, 35.37; H, 1.75; N, 24.70.

SUMMARY OF PROPERTIES

Appearance: Crimson prisms
Molecular formula: $C_{10}H_6N_6O_8$
Molecular weight: 338.19
Oxygen balance ($CO_2$ and $H_2O$): −71%
Nitrogen percentage: 24.85
Detonation velocity (calculated): 7.0 mm/$\mu$sec
Detonation pressure (calculated): 200 kbar
Melting point: 297° C. (decomposition)
Density (observed): 1.78 g/$cm^3$
Density (calculated): 1.79 g/$cm^3$
IMpact sensitivity ($H_{50}$) using a 2.5 kg type 12 tool: 35-27 cm The compound 2,6-diamino-1,4,5,8-tetranitronaphthalene may be utilized as an explosive in the same manner that other solid, crystalline explosive materials are utilized. The energy of this compound is comparable to TNT which has a detonation velocity of 6.96 mm/$\mu$sec and a detonation pressure of 205 kbar. Its density is significantly higher since the value for TNT is 1.65 g/$cm^3$. The compound 2,6-diamino-1,4,5,8-tetranitronaphthalene appears to be somewhat more sensitive to impact than TNT, preliminary data indicating impact sensitivity ($H_{50}$) of 35-37 cm with type 12 tools compared to 70-75 cm for TNT. On the other hand, the compound is quite thermally stable, showing decomposition at 297° C., without prior melting.

What is claimed is:

1. A compound 2,6-diamino-1,4,5,8-tetranitronaphthalene, with the structure:

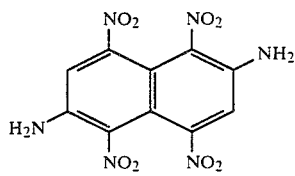

2. A method for preparing 2,6-diamino-1,4,5,8-tetranitronaphthalene comprising the steps of:
   A. converting a starting material of 2,6-dimethylnaphthalene into 2,6-naphthalene dicarboxylic acid;
   B. nitrating said 2,6-naphthalene dicarboxylic acid with $HNO_3$ to form 1,5-dinitro-3,7-naphthalene dicarboxylic acid;
   C. forming a suspension of said 1,5-dinitro-3,7-naphthalene dicarboxylic acid with $H_2SO_4$ and 1,2-dichloroethane and adding solid $NaN_3$ and NaOH to form 3,7-diamino-1,5-dinitronaphthalene;
   D. reacting said 3,7-diamino-1,5-dinitronaphthalene with trifluoroacetic anhydride to form 1,5-dinitro-3,7-di(trifluoroacetamido) naphthalene;

E. nitrating said 1,5-dinitro-3,7-di(trifluoroacetamido) naphthalene with $HNO_3$ and $H_2SO_4$ to form 2,6-di(trifluoroacetamido)-1,4,5,8-tetranitronaphthalene; and F. reacting said 2,6-di(trifluoroacetamido)-1,4,5,8-tetranitronaphthalene with methanol and dry hydrogen chloride to form 2,6-diamino-1,4,5,8-tetranitronaphthalene.

3. The method of claim 2 wherein the nitric acid of step B is 90% $HNO_3$.

4. The method of claim 2 wherein the nitration of step B is followed by heating to 60° C. over a one hour period and is maintained for an additional one hour, after which the mixture is allowed to cool to ambient temperature and poured over ice.

5. The method of claim 2 wherein the sulfuric acid of step C is 18–24% fuming $H_2SO_4$.

6. The method of claim 2 wherein the suspension of step C is followed by cooling to 3° C., prior to the addition of solid $NaN_3$ and NaOH.

7. The method of claim 2 wherein the addition of $NaN_3$ in step C is performed in a manner so as to avoid the mixture attaining a temperature greater than 8° C.

8. the method of claim 7 wherein the addition of $NaN_3$ is followed by allowing the mixture to cool to ambient temperature, heating to 50° C. for one hour, then cooling to 15° C.

9. The method of claim 8 wherein the cooling to 15° C. is followed by the addition of NaOH.

10. The method of claim 8 wherein the sodium hydroxide is 50% aqueous NaOH.

11. The method of claim 2 wherein the reaction of step D is refluxed for two days then cooled.

12. The method of claim 2 wherein the nitric acid of step E is 90% $HNO_3$.

13. The method of claim 2 wherein the sulfuric acid of step E is 97% $H_2SO_4$.

14. The method of claim 2 wherein the nitration of step E is followed by heating to 55° C. for two hours, after which the mixture is allowed to cool to ambient temperature and poured over ice.

15. The method of claim 2 wherein the reaction of step F is accomplished by bubbling dry hydrogen chloride, over a three hour period, into the mixture.

16. The method of claim 2 wherein the reaction of step F is followed by removal of the methanol under reduced pressure with a warm water bath.

* * * * *